United States Patent
Brabec et al.

(10) Patent No.: US 6,512,940 B1
(45) Date of Patent: Jan. 28, 2003

(54) SUBCUTANEOUS SPIRAL ELECTRODE FOR SENSING ELECTRICAL SIGNALS OF THE HEART

(75) Inventors: Scott J. Brabec, Elk River, MN (US); Kenneth R. Brennen, Fridley, MN (US); William Schindeldecker, Foreston, MN (US); James Strom, Arden Hills, MN (US)

(73) Assignee: Medtronic, Inc., Minneapolis, MN (US)

( * ) Notice: Subject to any disclaimer, the term of this patent is extended or adjusted under 35 U.S.C. 154(b) by 60 days.

(21) Appl. No.: 09/703,152

(22) Filed: Oct. 31, 2000

(51) Int. Cl.[7] .................................................. A61B 5/04
(52) U.S. Cl. ........................................ 600/374; 600/509
(58) Field of Search ................................. 600/372, 373, 600/374, 375, 376, 377, 509

(56) References Cited

U.S. PATENT DOCUMENTS

| | | | |
|---|---|---|---|
| 3,983,867 A | 10/1976 | Case ........................ 128/2.06 G |
| 4,023,565 A | 5/1977 | Ohlsson .................. 128/2.06 B |
| 4,082,086 A | 4/1978 | Page ................................ 128/2 |
| 4,121,576 A | 10/1978 | Greensite ............... 128/2.06 V |
| 4,170,227 A | 10/1979 | Feldman et al. ............ 128/704 |
| 4,263,919 A | 4/1981 | Levin ........................ 128/708 |
| 4,310,000 A | 1/1982 | Lindemans ........... 128/419 PG |
| 4,313,443 A | 2/1982 | Lund .......................... 128/642 |
| 4,476,868 A | 10/1984 | Thompson ............ 128/419 PG |
| 4,593,702 A | 6/1986 | Kepski et al. ............... 128/696 |
| 4,674,508 A | 6/1987 | Decote .................. 128/419 PT |
| 4,729,376 A | 3/1988 | Decote, Jr. ............. 128/419 PT |
| 5,052,388 A | 10/1991 | Sivula et al. .......... 128/419 PG |
| 5,331,966 A | 7/1994 | Bennett et al. ............. 128/696 |
| 5,345,362 A | 9/1994 | Winkler ...................... 361/681 |
| 6,108,577 A | 8/2000 | Benser ........................ 600/517 |
| 6,272,379 B1 | 8/2001 | Fischell et al. ................. 607/5 |

FOREIGN PATENT DOCUMENTS

| | | |
|---|---|---|
| EP | 0 460 324 A2 | 12/1991 |
| EP | 0 472 411 A1 | 2/1992 |
| EP | 0 941 695 A2 | 9/1999 |
| WO | WO 01/70331 A2 | 9/2001 |

*Primary Examiner*—Scott M. Getzow
(74) *Attorney, Agent, or Firm*—Girma Wolde-Michael; Michael C. Soldner

(57) ABSTRACT

An implantable pacemaker is provided with subcutaneous spiral electrodes for sensing electrical signals of the heart. Subcutaneous spirals or spiral electrodes are embedded individually into three or four recessed casings placed in a compliant surround that is attached to the perimeter of the implanted medical device. The electrodes are electrically connected to the circuitry of the implanted pacemaker and detect cardiac depolarization waveforms displayable as electrocardiographic tracings on an external instrument such as a programmer. The spiral electrode constitutes the proximal end of a continuous wire that upon egress from the recessed casing is insulated using insulative material.

26 Claims, 9 Drawing Sheets

SUBCUTANEOUS SPIRAL ELECTRODE FOR SENSING ELECTRICAL SIGNALS OF THE HEART

FIELD OF THE INVENTION

The present invention relates generally to implantable pacemakers and more particularly to a subcutaneous electrode used to sense, record, and acquire electrocardiographic data and waveform tracings from an implanted pacemaker without the need for or use of surface (skin) electrodes. More particularly, the present invention relates to spiral electrodes placed into recesses incorporated within a compliant, insulative "surround." Each spiral electrode becomes an integral element of a Subcutaneous Electrode Array or SEA that, in turn, detects cardiac depolarizations communicable and displayable by a portable device programmer.

BACKGROUND OF THE INVENTION

The electrocardiogram (ECG) is commonly used in medicine to determine the status of the electrical conduction system of the human heart. As practiced, an ECG recording device is commonly attached to the patient via ECG leads connected to pads arrayed on the patient's body so as to achieve a recording that displays the cardiac waveforms in any one of 12 possible vectors.

Since the implantation of the first cardiac pacemaker, implantable medical device technology has advanced with the development of sophisticated, programmable cardiac pacemakers, pacemaker-cardioverter-defibrillator arrhythmia control devices and drug administration devices designed to detect arrhythmias and apply appropriate therapies. The detection and discrimination between various arrhythmic episodes in order to trigger the delivery of an appropriate therapy is of considerable interest. Prescription for implantation and programming of the implanted device are based on the analysis of the PQRST electrocardiogram (ECG) and the electrogram (EGM). The waveforms are usually separated for such analysis into the P-wave and R-wave in systems that are designed to detect the depolarization of the atrium and ventricle respectively. Such systems employ detection of the occurrence of the P-wave and R-wave, analysis of the rate, regularity, and onset of variations in the rate of recurrence of the P-wave and R-wave, the morphology of the P-wave and R-wave and the direction of propagation of the depolarization represented by the P-wave and R-wave in the heart. The detection, analysis and storage of such EGM data within implanted medical devices are well known in the art. Acquisition and use of ECG tracing (s), on the other hand, has generally been limited to the use of an external ECG recording machine attached to the patient via surface electrodes of one sort or another.

The aforementioned ECG systems that utilize detection and analysis of the PQRST complex are all dependent upon the spatial orientation and number of electrodes available near or around the heart to pick up the depolarization wave front.

As the functional sophistication and complexity of implantable medical device systems increased over the years, it has become increasingly more important for such systems to include a system for facilitating communication between one implanted device and another implanted device and/or an external device, for example, a programming console, monitoring system, or the like. For diagnostic purposes, it is desirable that the implanted device be able to communicate information regarding the device's operational status and the patient's condition to the physician or clinician. State of the art implantable devices are available which can even transmit a digitized electrical signal to display electrical cardiac activity (e.g., an ECG, EGM, or the like) for storage and/or analysis by an external device. The surface ECG, however, has remained the standard diagnostic tool since the very beginning of pacing and remains so today.

To diagnose and measure cardiac events, the cardiologist has several tools from which to choose. Such tools include twelve-lead electrocardiograms, exercise stress electrocardiograms, Holter monitoring, radioisotope imaging, coronary angiography, myocardial biopsy, and blood serum enzyme tests. Of these, the twelve-lead electrocardiogram (ECG) is generally the first procedure used to determine cardiac status prior to implanting a pacing system; thereafter, the physician will normally use an ECG available through the programmer to check the pacemaker's efficacy after implantation. Such ECG tracings are placed into the patient's records and used for comparison to more recent tracings. It must be noted, however, that whenever an ECG recording is required (whether through a direct connection to an ECG recording device or to a pacemaker programmer), external electrodes and leads must be used.

Unfortunately, surface electrodes have some serious drawbacks. For example, electrocardiogram analysis performed using existing external or body surface ECG systems can be limited by mechanical problems and poor signal quality. Electrodes attached externally to the body are a major source of signal quality problems and analysis errors because of susceptibility to interference such as muscle noise, power line interference, high frequency communication equipment interference, and baseline shift from respiration. Signal degradation also occurs due to contact problems, ECG waveform artifacts, and patient discomfort. Externally attached electrodes are subject to motion artifacts from positional changes and the relative displacement between the skin and the electrodes. Furthermore, external electrodes require special skin preparation to ensure adequate electrical contact. Such preparation, along with positioning the electrode and attachment of the ECG lead to the electrode needlessly prolongs the pacemaker follow-up session. One possible approach is to equip the implanted pacemaker with the ability to detect cardiac signals and transform them into a tracing that is the same as or comparable to tracings obtainable via ECG leads attached to surface electrodes.

It is known in the art to monitor electrical activity of the human heart for diagnostic and related medical purposes. U.S. Pat. No. 4,023,565 issued to Ohlsson describes circuitry for recording ECG signals from multiple lead inputs. Similarly, U.S. Pat. No. 4,263,919 issued to Levin, U.S. Pat. No. 4,170,227 issued to Feldman, et al, and U.S. Pat. No. 4,593,702 issued to Kepski, et al, describe multiple electrode systems that combine surface EKG signals for artifact rejection.

The primary use for multiple electrode systems in the prior art appears to be vector cardiography from ECG signals taken from multiple chest and limb electrodes. This is a technique whereby the direction of depolarization of the heart is monitored, as well as the amplitude. U.S. Pat. No. 4,121,576 issued to Greensite discusses such a system.

Numerous body surface ECG monitoring electrode systems have been employed in the past in detecting the ECG and conducting vector cardiographic studies. For example, U.S. Pat. No. 4,082,086 issued to Page, et al., discloses a four electrode orthogonal array that may be applied to the patient's skin both for convenience and to ensure the precise orientation of one electrode to the other. U.S. Pat. No. 3,983,867 issued to Case describes a vector cardiography system employing ECG electrodes disposed on the patient in normal locations and a hex axial reference system orthogonal display for displaying ECG signals of voltage versus time generated across sampled bipolar electrode pairs.

U.S. Pat. No. 4,310,000 to Lindemans and U.S. Pat. Nos. 4,729,376 and 4,674,508 to DeCote, incorporated herein by reference, disclose the use of a separate passive sensing reference electrode mounted on the pacemaker connector block or otherwise insulated from the pacemaker case in order to provide a sensing reference electrode that is not part of the stimulation reference electrode and thus does not have residual after-potentials at its surface following delivery of a stimulation pulse.

Moreover, in regard to subcutaneously implanted EGM electrodes, the aforementioned Lindemans U.S. Pat. No. 4,310,000 discloses one or more reference sensing electrode positioned on the surface of the pacemaker case as described above. U.S. Pat. No. 4,313,443 issued to Lund describes a subcutaneously implanted electrode or electrodes for use in monitoring the ECG.

U.S. Pat. No. 5,331,966 to Bennett, incorporated herein by reference, discloses a method and apparatus for providing an enhanced capability of detecting and gathering electrical cardiac signals via an array of relatively closely spaced subcutaneous electrodes (located on the body of an implanted device).

Patent application Ser. No. 09/697,438, entitled, "Surround Shroud Connector And Electrode Housings For A Subcutaneous Electrode Array And Leadless ECGs," by Ceballos et al., incorporated herein by reference, discloses an apparatus for providing a compliant surround circumferentially placed around the pacemaker's perimeter and equipped with recesses for various types of electrodes used to detect cardiac depolarization waves. It is in conjunction with this compliant shroud that the present invention is practiced.

SUMMARY OF THE INVENTION

The present invention encompasses a Subcutaneous Electrode Spiral, Spiral Electrode, as a preferred embodiment, that is embedded individually into three or four recessed casings placed in a compliant surround that is attached to the perimeter of an implanted pacemaker. These electrodes are electrically connected to the circuitry of the implanted pacemaker and detect cardiac depolarization waveforms displayable as electrocardiographic tracings on the pacemaker Programmer screen when the programming head is positioned above an implanted pacemaker (or other implanted device) so equipped with a leadless Subcutaneous Electrode Array (SEA).

The recessed casing is composed of a polymer. This casing has walls into which body fluid is allowed to flow so that the body fluid is above and around the spiral, spiral coil, which is maintained within the casing by a small circumferential well constructed into the base of the recessed casing. The spiral coil may be constructed from any of the titanium group of metals, as well as platinum, platinum alloys, or any of the platinum group of metals with or without alloying components. This spiral coil constitutes the proximal end of a continuous wire that, upon egress from the recessed casing, is insulated by tubular, insulative material such as silicone. The insulated tubular wiring fits into channel(s) located on the inner arc of the aforementioned compliant surround. The distal end of this wire is welded to a connector feedthrough assembly in contact with amplifier(s) in the microprocessor circuitry.

The present invention is designed to solve several problems that may be encountered in the use of subcutaneous electrodes generally. The electrical potentials from the cardiac depolarizations are very small, in the order of tens of microvolts. As a result, the signal that reaches the electrodes may have a low slew rate. Solid, plate electrodes exhibit noise spikes and potential drifts that are large in comparison to the cardiac signals. These plate electrodes themselves may be the major contributors to such noise. Contamination of electrode surfaces at the molecular level may cause extraneous voltage excursions large enough to interfere with the sensing function. Motion artifacts from the perturbation caused by fluid or tissue motion next to the surface has been demonstrated in tank tests, and represents a commonly observed phenomenon.

The present invention, in its preferred embodiment, solves these issues in that it is a spiral, subcutaneous electrode that can be attached to a pulse generator via a compliant surround and provide a reliable response. The electrode has a large surface area, is manufactured from low cost materials, and can be assembled in an inexpensive way. The surface of the electrode has no direct contact with body tissue and moving body fluids, but it is treated with electrode coatings such as platinum black or titanium nitride to enhance its signal-conducting and depolarization properties. Such enhancing coatings are important since, as time passes, the pacemaker and, with it, the electrodes become encapsulated in scar tissue and thus come into indirect contact with the body tissue. Even indirect tissue contact may have a damping effect on the detection ability of the electrode if not treated with enhancing coatings.

The electrode, as designed, affords a continuous wire connection, without weld or bonds on the electrode surface. Moreover, the electrode is anchored in the device free of any chemical bonding that might cause potential excursions due to electro active species being released to the electrode surface. The portion of the electrode covered by the recessed casing is minimal thereby preventing any potential excursions caused by fluid creep or by trapped oxygen or hydrogen gradients, or $P_h$ gradients. A second embodiment of the present invention employs a coiled electrode design that is manufactured in a rectangular configuration. This electrode has all the same electrical and signal detection properties as the spiral electrode and is constructed of the same materials and has the same enhancing coatings.

A third embodiment of the present invention uses a flat plated electrode embedded within the well of the recessed casing. To mechanically stabilize the electrode and reduce the possibility of electro kinetic potential disturbances on the electrode (due to tissue or fluid motion artifact), the bottom of the recess or well is patterned with a cross hatch of elevations and depressions with a minimum of contact area between the plate and the polymer used in the recessed casing. The purpose of the cross-hatch is to support the electrode and provide fluid contact to the underside of the electrode interface.

A protective cap, vented to allow fluid ingress to the active electrode element, may be placed over the well containing the flat electrode. This cap applies pressure on the electrode, pressing it against the textured bottom of the recess or well, thus preventing motion of the electrode. This cap also serves to dampen any external fluid motion that might otherwise reach the electrode and cause electro kinetic potential transients. The electrodes' surfaces require protection during handling as well as to prevent contamination. A coating, such as may be provided by Dexamethazone Sodium Phosphate, provides such protection as well as enhancing the wetting of the electrode surface after implant. Conductive hydro gels, applied wet and allowed to dry, may also be applied to the electrode surfaces to protect them from damage during handling and prevent contamination.

The spacing of the electrodes in the present invention around the compliant surround provides maximal electrode spacing and, at the same time, appropriate insulation from the pacemaker casing due to the insulative properties of the surround and the cup recesses into which the electrodes are placed. The positioning maintains a maximum and equal distance between the electrode pairs. Such spacing with the four-electrode embodiment maintains the maximum average signal due to the fact that the spacing of the two vectors is equal and the angle between these vectors is 90°, as is shown in mathematical modeling. Such orthogonal spacing of the electrode pairs also minimizes signal variation. An alternate three-electrode embodiment has the electrodes arranged within the shroud in an equilateral triangle along the perimeter of the implanted pacemaker. Vectors in this embodiment can be combined to provide adequate sensing of cardiac signals (ECGs).

The present invention allows the physician or medical technician to perform leadless follow-up that, in turn, eliminates the time it takes to attach external leads to the patient. Such timesavings can reduce the cost of follow-up, as well as making it possible for the physician or medical technician to see more patients during each day. Though not limited to these, other uses include: Holter monitoring with event storage, arrhythmia detection and monitoring, capture detection, ischemia detection and monitoring (S-T elevation and suppression on the ECG), changes in QT interval, and transtelephonic monitoring.

DETAILED DESCRIPTION OF THE DRAWINGS

Figure 1:
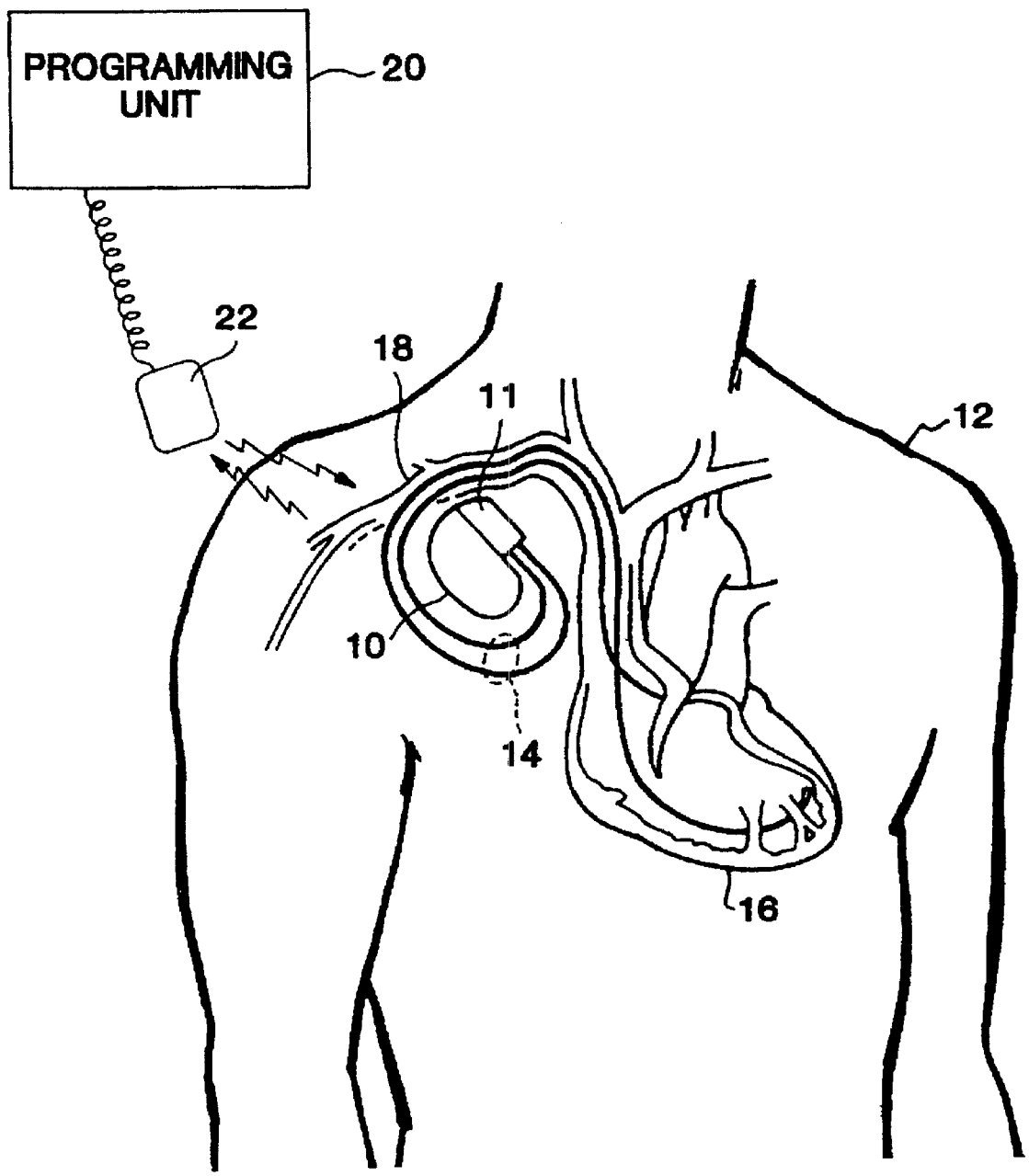
FIG. 1 is an illustration of a body-implantable device system in accordance with the present invention, including a hermetically sealed device implanted in a patient and an external programming unit.

FIG. 1 is an illustration of an implantable medical device system adapted for use in accordance with the present invention. The medical device system shown in FIG. 1 includes an implantable device 10—a pacemaker in this embodiment—which has been implanted in a patient 12. In accordance with conventional practice in the art, pacemaker 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with its distal end situated in the atrium and/or ventricle of heart 16.

Although the present invention will be described herein in one embodiment which includes a pacemaker, those of ordinary skill in the art having the benefit of the present disclosure will appreciate that the present invention may be advantageously practiced in connection with numerous other types of implantable medical device systems, and indeed in any application in which it is desirable to provide a communication link between two physically separated components.

Also depicted in FIG. 1 is an external programming unit 20 for non-invasive communication with implanted device 10 via uplink and downlink communication channels, to be hereinafter described in further detail. Associated with programming unit 20 is a programming head 22, in accordance with conventional medical device programming systems, for facilitating two-way communication between implanted device 10 and programmer 20. In many known implantable device systems, a programming head such as that depicted in FIG. 1 is positioned on the patient's body over the implant site of the device (usually within 2- to 3-inches of skin contact), such that one or more antennae within the head can send RF signals to, and receive RF signals from, an antenna disposed within the hermetic enclosure of the implanted device or disposed within the connector block of the device, in accordance with common practice in the art.

Figure 2:
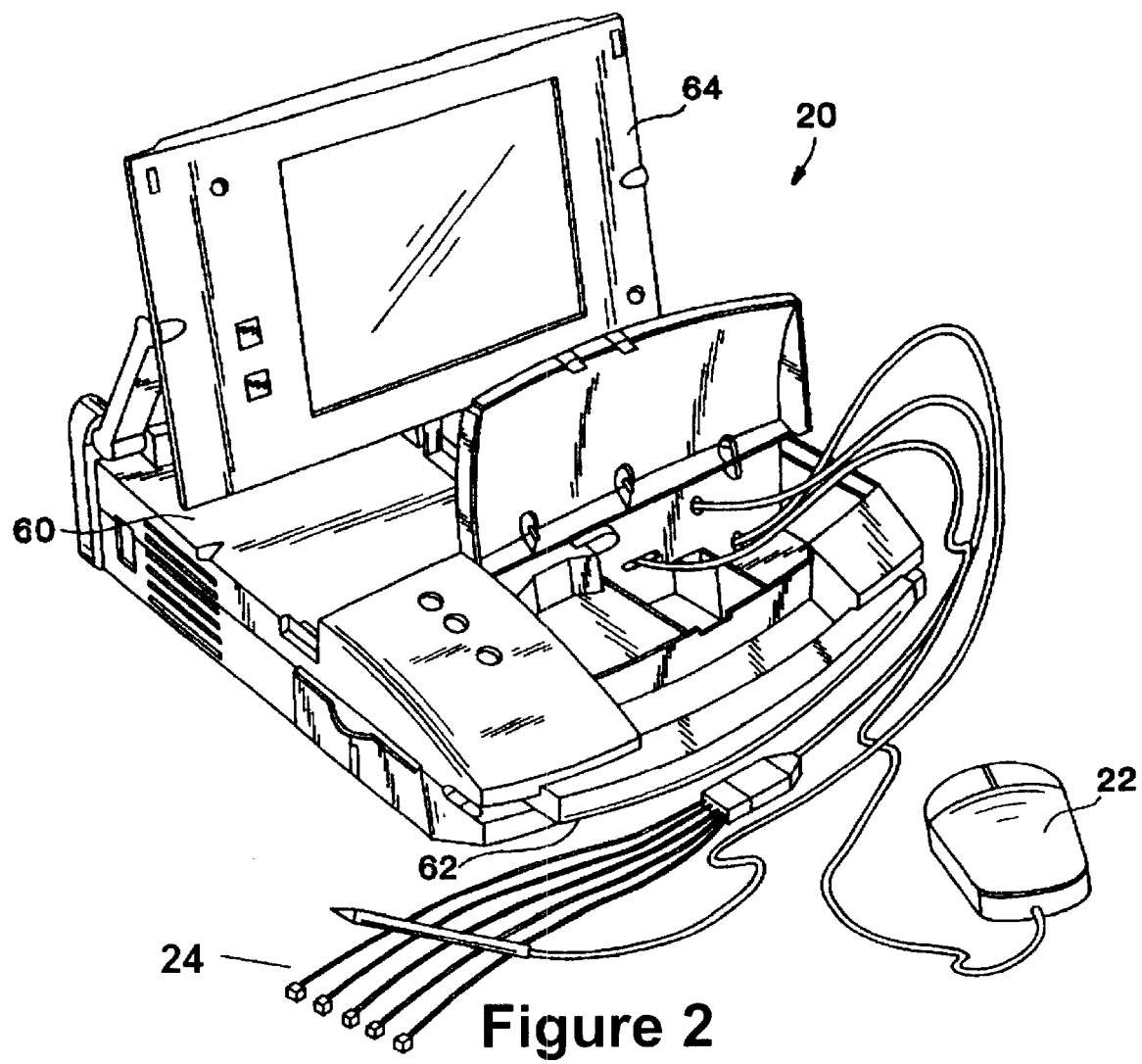
FIG. 2 is a perspective view of the external programming unit of FIG. 1.

In FIG. 2, there is shown a perspective view of programming unit 20 in accordance with the presently disclosed invention. Internally, programmer 20 includes a processing unit (not shown in the Figures) that in accordance with the presently disclosed invention is a personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well-known to those of ordinary skill in the art.

Referring to FIG. 2, programmer 20 comprises an outer housing 60, which is preferably made of thermal plastic or another suitably rugged yet relatively light-weight material. A carrying handle, designated generally as 62 in FIG. 2, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof.

A floppy disk drive is disposed within housing 60 and is accessible via a disk insertion slot (not shown). A hard disk drive is also disposed within housing 60, and it is contemplated that a hard disk drive activity indicator, (e.g., an LED, not shown) could be provided to give a visible indication of hard disk activation.

As would be appreciated by those of ordinary skill in the art, it is often desirable to provide a means for determining the status of the patient's conduction system. Normally, programmer 20 is equipped with external ECG leads 24. It is these leads which are rendered redundant by the present invention.

In accordance with the present invention, programmer 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

In the perspective view of FIG. 2, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

As would be appreciated by those of ordinary skill in the art, display screen 64 is operatively coupled to the computer circuitry disposed within housing 60 and is adapted to provide a visual display of graphics and/or data under control of the internal computer.

Programmer 20 described herein with reference to FIG. 2 is described in more detail in U.S. Pat. No. 5,345,362 issued to Thomas J. Winkler, entitled "Portable Computer Apparatus With Articulating Display Panel," which patent is hereby incorporated herein by reference in its entirety. The Medtronic Model 9790 programmer is the implantable device-programming unit with which the present invention may be advantageously practiced.

Figure 3:
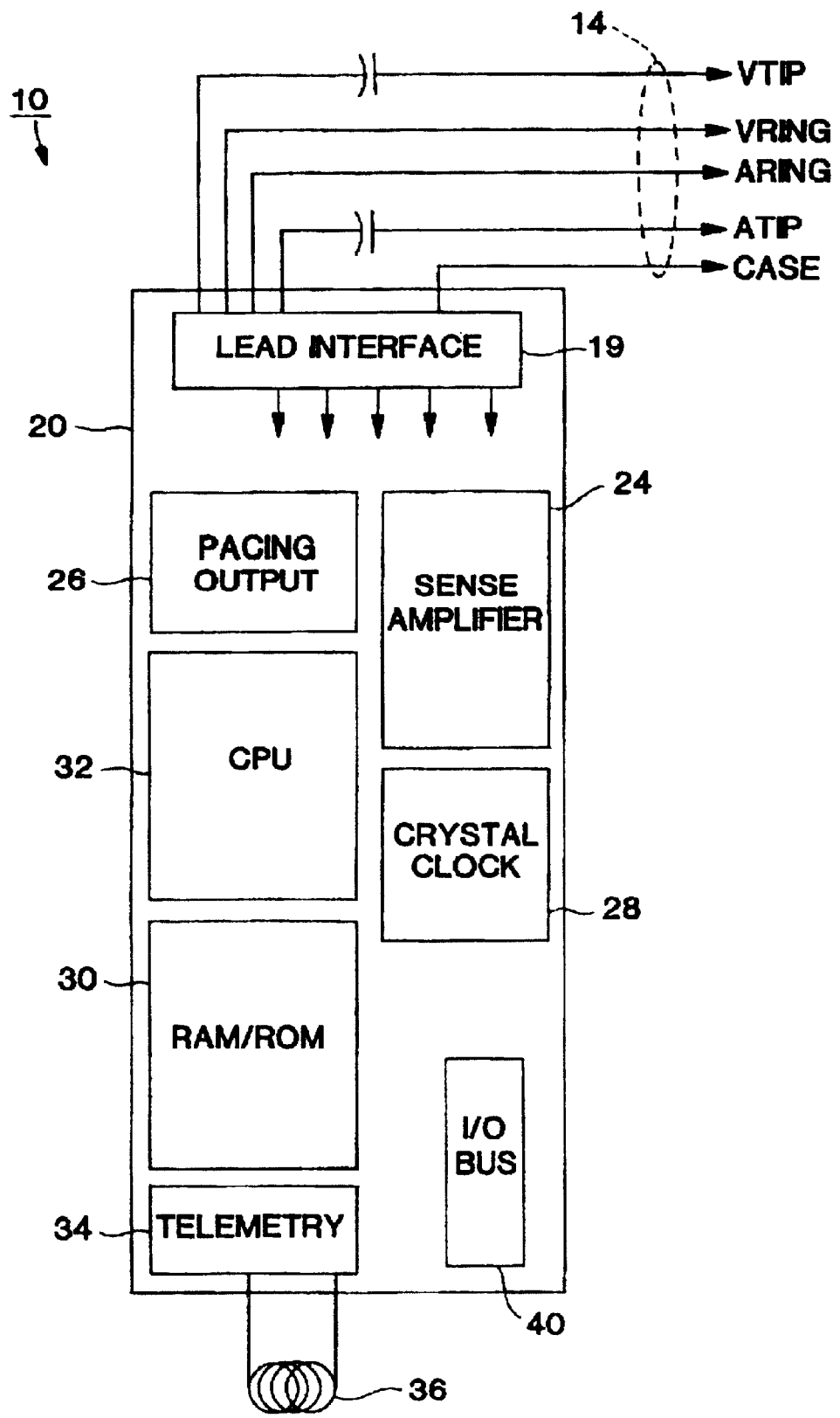
FIG. 3 is a block diagram of the implanted device from FIG. 1.

FIG. 3 is a block diagram of the electronic circuitry that makes up pulse generator 10 in accordance with the presently disclosed invention. As can be seen from FIG. 3, pacemaker 10 comprises a primary stimulation control circuit 20 for controlling the device's pacing and sensing functions. The circuitry associated with stimulation control circuit 20 may be of conventional design, in accordance, for example, with what is disclosed Pat. No. 5,052,388 issued to Sivula et al., "Method and apparatus for implementing activity sensing in a pulse generator." To the extent that certain components of pulse generator 10 are conventional in their design and operation, such components will not be described herein in detail, as it is believed that design and implementation of such components would be a matter of routine to those of ordinary skill in the art. For example, stimulation control circuit 20 in FIG. 3 includes sense amplifier circuitry 24, stimulating pulse output circuitry 26, a crystal clock 28, a random-access memory and read-only memory (RAM/ROM) unit 30, and a central processing unit (CPU) 32, all of which are well-known in the art.

Pacemaker 10 also includes internal communication circuit 34 so that it is capable communicating with external programmer/control unit 20, as described in FIG. 2 in greater detail.

With continued reference to FIG. 3, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional connector block assembly 11, shown in FIG. 1. Electrically, the coupling of the conductors of leads and internal electrical components of pulse generator 10 may be facilitated by means of a lead interface circuit 19 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pulse generator 10 are not shown in FIG. 3, although it will be clear to those of ordinary skill in the art that, for example, leads 14 will necessarily be coupled, either directly or indirectly, to sense amplifier circuitry 24 and stimulating pulse output circuit 26, in accordance with common practice, such that cardiac electrical signals may be conveyed to sensing circuitry 24, and such that stimulating pulses may be delivered to cardiac tissue, via leads 14. Also not shown in FIG. 3 is the protection circuitry commonly included in implanted devices to protect, for example, the sensing circuitry of the device from high voltage stimulating pulses.

As previously noted, stimulation control circuit 20 includes central processing unit 32 which may be an off-the-shelf programmable microprocessor or micro controller, but in the present invention is a custom integrated circuit. Although specific connections between CPU 32 and other components of stimulation control circuit 20 are not shown in FIG. 3, it will be apparent to those of ordinary skill in the art that CPU 32 functions to control the timed operation of stimulating pulse output circuit 26 and sense amplifier circuit 24 under control of programming stored in RAM/ROM unit 30. It is believed that those of ordinary skill in the art will be familiar with such an operative arrangement.

With continued reference to FIG. 3, crystal oscillator circuit 28, in the presently preferred embodiment a 32,768-Hz crystal controlled oscillator, provides main timing clock signals to stimulation control circuit 20. Again, the lines over which such clocking signals are provided to the various timed components of pulse generator 10 (e.g., microprocessor 32) are omitted from FIG. 3 for the sake of clarity.

It is to be understood that the various components of pulse generator 10 depicted in FIG. 3 are powered by means of a battery (not shown) which is contained within the hermetic enclosure of pacemaker 10, in accordance with common practice in the art. For the sake of clarity in the Figures, the battery and the connections between it and the other components of pulse generator 10 are not shown.

Stimulating pulse output circuit 26, which functions to generate cardiac stimuli under control of signals issued by CPU 32, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits that would be suitable for the purposes of practicing the present invention.

Sense amplifier circuit 24, which is of conventional design, functions to receive electrical cardiac signals from leads 14 and to process such signals to derive event signals reflecting the occurrence of specific cardiac electrical events, including atrial contractions (P-waves) and ventricular contractions (R-waves). CPU provides these event-indicating signals to CPU 32 for use in controlling the synchronous stimulating operations of pulse generator 10 in accordance with common practice in the art. In addition, these event-indicating signals may be communicated, via uplink transmission, to external programming unit 20 for visual display to a physician or clinician.

Those of ordinary skill in the art will appreciate that pacemaker 10 may include numerous other components and subsystems, for example, activity sensors and associated circuitry. The presence or absence of such additional components in pacemaker 10, however, is not believed to be pertinent to the present invention, which relates primarily to the implementation and operation of communication subsystem 34 in pacemaker 10, and an associated communication subsystem in external unit 20.

Figure 4:
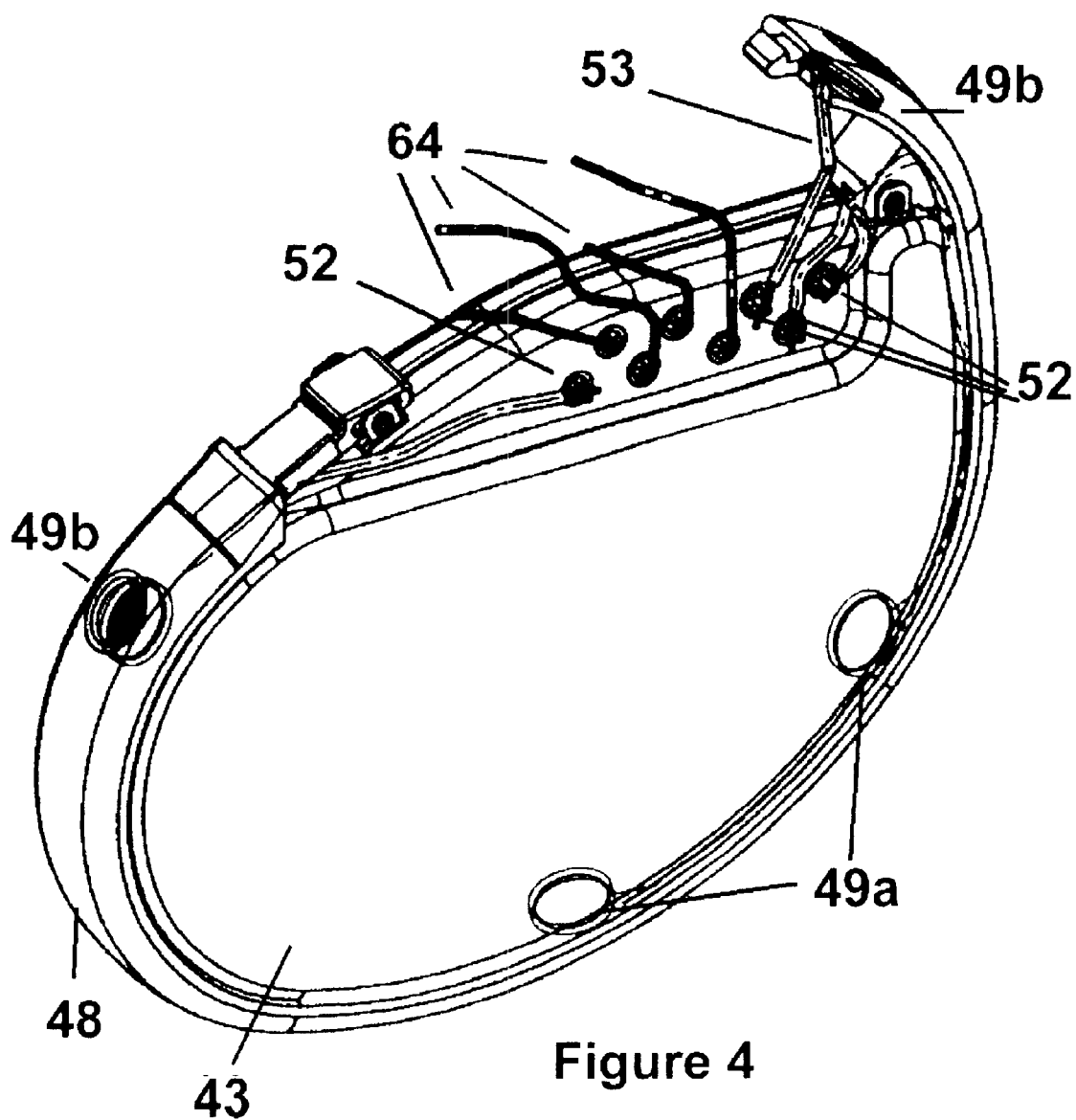
FIG. 4 is a sectional view of surround shroud displaying electrical connections of the electrodes to the hybrid circuitry.

FIG. 4 is a sectional view of surround shroud 48 displaying electrical connections of the electrodes to the hybrid circuitry surrounded by insulators 43. Surround displays recessed cups 49b and electrical contacts 49a all of which are connected to the hybrid circuitry (not shown) via tubular wiring 53. Tubular wiring 53 is welded to feedthrough contacts 52 located on upper portion of the board holding the hybrid circuitry. Other contacts 64 electrically connect the atrial and ventricular pacing lead tip and ring to the hybrid circuitry.

Figure 5:
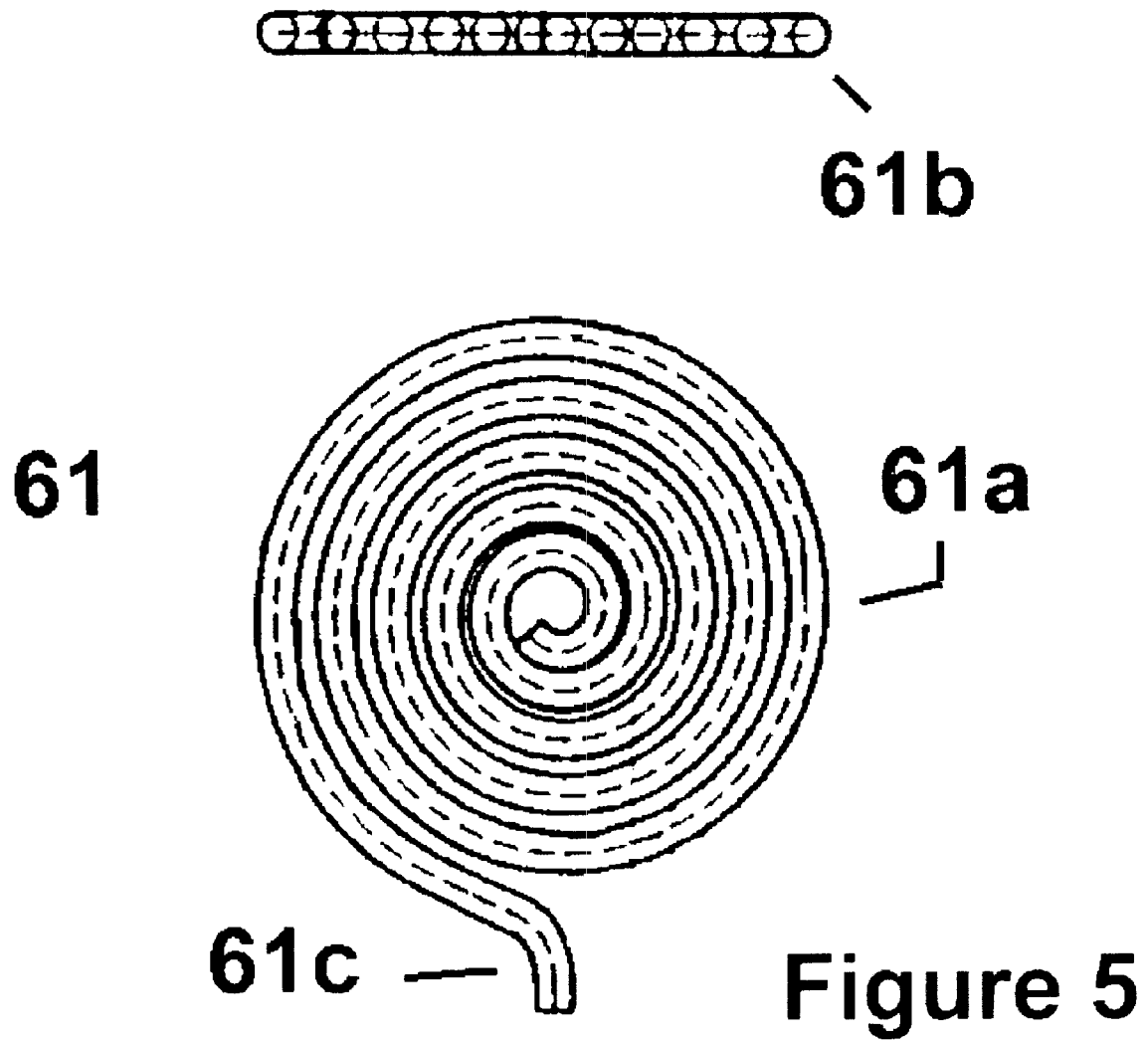
FIG. 5 is a cross sectional view of a spiral coil, which is one embodiment of an electrode practiced in the present invention.

FIG. 5 is a cross sectional view of spiral coil 61, which is the preferred embodiment of an electrode practiced in the present invention. Spiral coil 61 consists of a wire of titanium or any of the titanium group of metals, platinum, platinum alloy, or any platinum group of metals whose surface may be treated by sputtering, platinization, ion milling, sintering, etching, or a combination of these processes to create a large specific surface area. Spiral coil 61a is designed to fit into recessed well 49c (see FIG. 6), within which spiral coil 61b rests. The protruding end of spiral coil 61c is manufactured continuous with tubular wiring 53 (see FIG. 6). The one-piece continuous design eliminates an additional weld or connection at the actual electrode. The elimination of the weld in this area is significant, because it eradicates the possibility of two dissimilar metals interacting within the ionic environment and adding an erroneous signal to the system. Removing the weld also eliminates any intermetalics formed during the weld.

Figure 6:
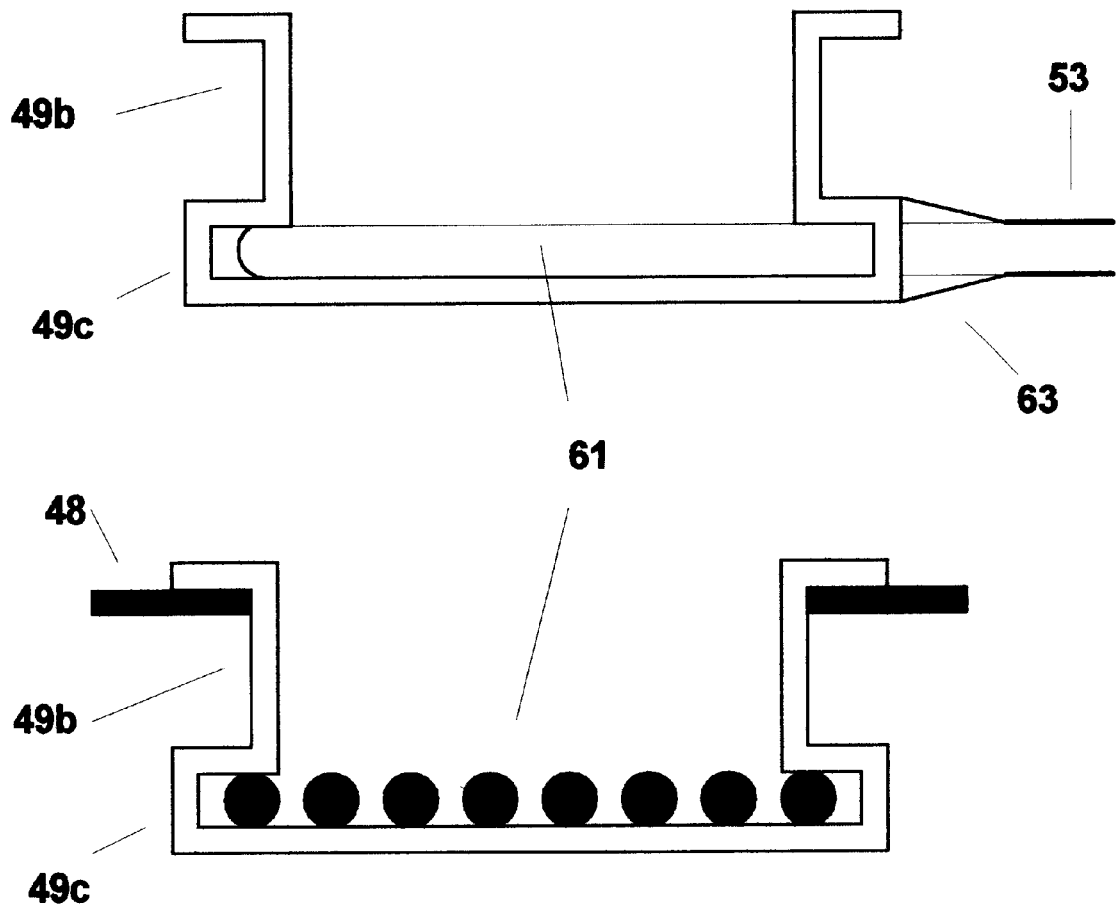
FIG. 6 is a cross sectional view of spiral coil housed in a well at the base of a recessed casing.

FIG. 6 is a cross sectional view of spiral coil 61 fitted into well 49c at the base of recessed cup 49b that is fitted into compliant shroud 48 (see FIG. 4). Thin film coatings via sputtering (porous TiN), platinization (platinum black), or applications of RuO, ion milling, sintering, etching, or a combination of these processes to create a large specific surface area may be used to treat the surface of spiral coil wire 61. Larger surface areas decrease the interfacial impedance, thereby allowing lower impedances at lower frequencies, thereby increase the signal-to-noise ratio. Wire is manufactured of any of the titanium group of metals, as well as platinum, platinum alloy, or any of the platinum group of metals, with or without alloying components.

The spaces around spiral coil 61 allow body fluid to flow around, between, and below the metal coils. Body fluids have conductive properties that allow cardiac depolarization waves to reach spiral electrode 61. The depolarization waves are detected as changes in electrical potential and transmitted via continuous tubular wire protected by insulator 63 as wire exits well 49c. Tubular material 53 keeps the wire insulated from other electrical potentials and protects the continuous wire. This continuous, conductive wire carries the signal(s) to the amplifier(s), hybrid circuitry, and microprocessor for processing and conversion into ECG tracings that may be printed by the printer located in programmer 20 (see FIG. 2). Compliant shroud 48 (see FIG. 4) serves to maintain the recessed cup in position relative to other coils which spacing is required for orthogonal or equilateral detection of the cardiac depolarization waves.

Figure 7:
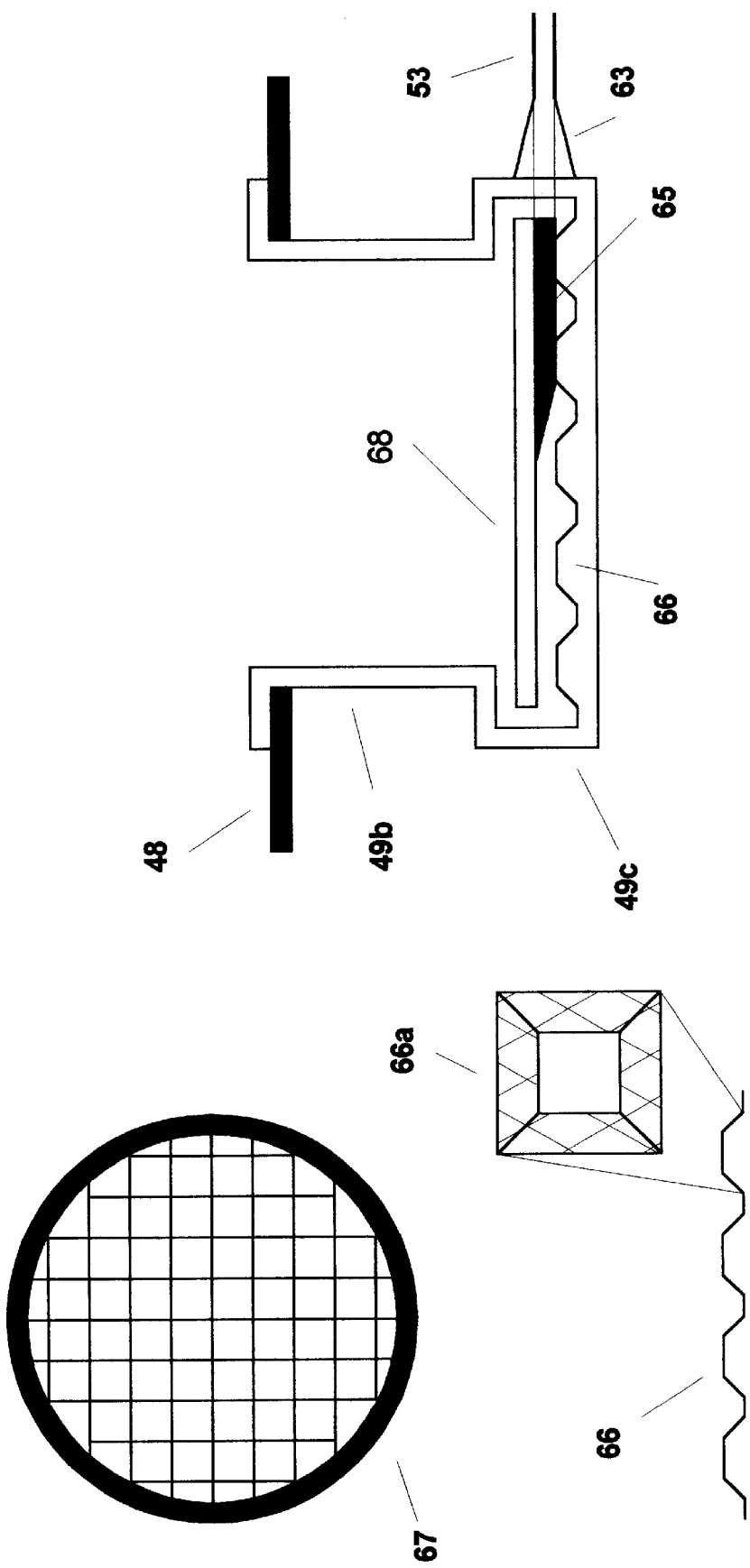
FIG. 7 is a cross sectional view of a recessed cup that employs a cross hatch of elevations and depressions in the well at the base of the cup.

FIG. 7 is a cross sectional view of a recessed cup that employs a crosshatch of elevations and depressions 66 in well 49c at base of recessed cup 49b. These elevations and depressions are continuous with the polymer used in the recessed up and well. An alternative electrode embodiment, which may be used with the crosshatched base, employs a thin, solid, spherical electrode 68 that lies on top of crosshatch 66. Viewed from above, crosshatch 67 would appear as shown. Viewed again from above, individual elevations 66a appear as shown on the inset drawing. Turning again to the crosshatch, elevations and depressions 66 mechanically stabilize the electrode and reduce the possibility of electro kinetic potential disturbances on the electrode (tissue or fluid motion artifact). The pattern of crosshatched elevations and depressions provide a minimum contact area between the wire and the polymer used to form the recessed cup 49b and well 49c. The purpose of the crosshatch is to support electrode 68 while providing fluid contact around, between, and below underside of electrode. Body fluids have conductive properties that allow cardiac depolarization waves to reach electrode 68. Since thin, solid, spherical electrode 68 is not continuous with tubular wiring 53, small metal plate 65 bonded or welded to tubular wiring 53 is welded to underside of electrode 68.

Cardiac depolarization waves are detected as changes in electrical potential and transmitted via continuous tubular wire protected by insulator 63 as wire exits well 49c. A tubular material 53 that keeps the wire insulated from other electrical potentials then protects the continuous wire. This conductive wire carries the signal(s) to the amplifier(s), hybrid circuitry, and microprocessor for processing and conversion into ECG tracings that are printed by the printer located in programmer 20 (FIG. 2). Compliant shroud 48 (see FIG. 4) serves to maintain the recessed cup in position relative to other coils which spacing is required for orthogonal or equilateral detection of the cardiac depolarization waves.

Figure 8:
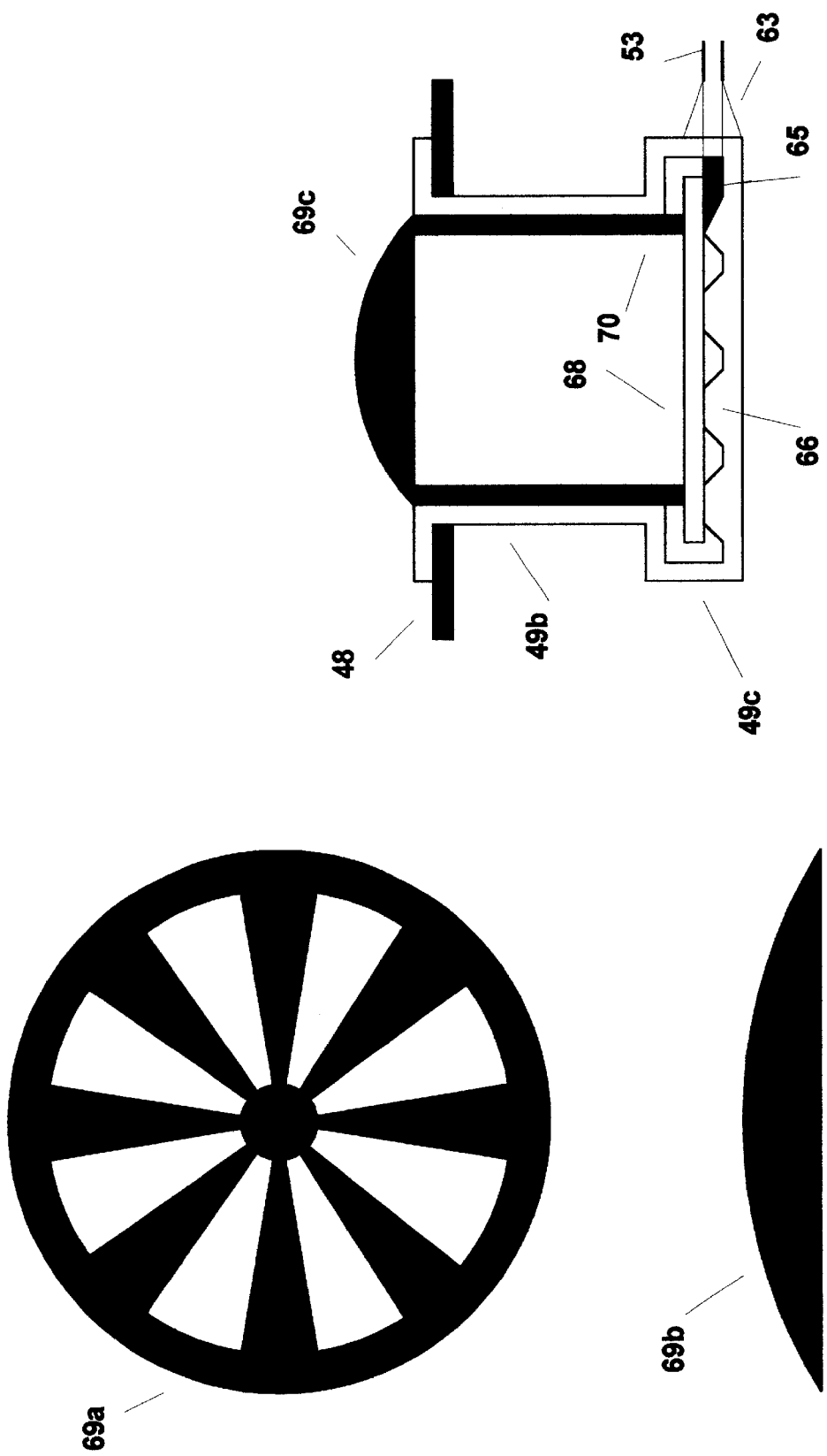
FIG. 8 is a cross sectional view of a vented protective cap fitting over and into the recessed cup.

FIG. 8 is a cross sectional view of vented protective cap 69a fitted over and into recessed cup 49b. Protective cap 69a is vented to allow fluid ingress to the active electrode element and is placed over the well 69c containing active electrode 68. This cap slides into recessed cup 49b, contacts electrode 68 and applies pressure 70 on the electrode, pressing it against the crosshatched bottom 66 of well 49c, thus preventing motion of the electrode. The cap, constructed of a polymer such as urethane, also serves to dampen any external fluid motion that might otherwise reach the active element and cause electro kinetic potential transients. A preferred design for the openings in the cap is one in which the support elements all run perpendicular to the elements of the coiled wire, i.e., radially as shown in the drawing 69a.

The ribs in cross section 69b are rounded on top to eliminate sharp edges, presenting a smooth appearance. The outer diameter of the protective cap is sized to provide a sliding fit 69c into the well containing the electrode. The protective cap may then be bonded to the wall of the recessed casing 49b with a suitable bonding agent. The cap and the electrode well must accommodate the wire 53 leading to the hybrid circuitry. A small opening in the side of the recessed casing serves to carry tubular wire from electrode to hybrid circuitry. Insulator 63 serves as anchor for wire 53 while the bonding material to small metal plate 65 serves as a seal.

Figure 9:
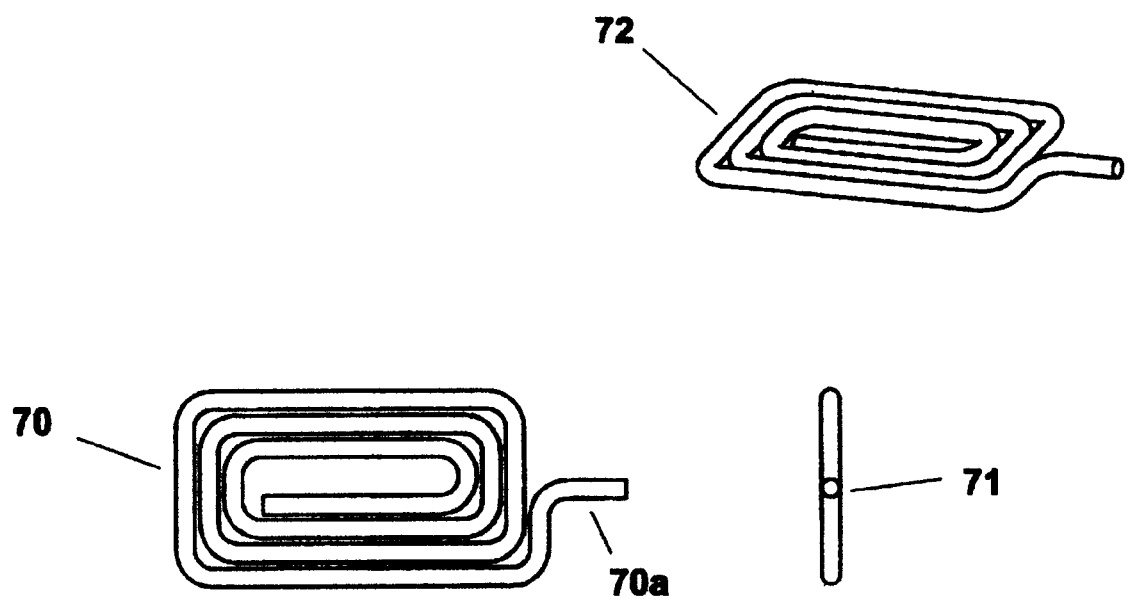
FIG. 9 is a cross sectional view of a rectangular coil electrode according to an alternate embodiment of the present invention.

FIG. 9 shows a cross sectional view of rectangular coil electrode 70 and 71, as well as a perspective view 72 of the same electrode which is an alternative embodiment of the present invention. Rectangular coil 70 consists of a wire of titanium or any of the titanium group of metals, platinum, platinum alloy, or any platinum group of metals whose surface may be treated by sputtering, platinization, ion milling, sintering, etching, or a combination of these processes to create a large specific surface area. Rectangular coil 70 is designed to fit into a rectangular recessed well 49c (modified from that shown in FIG. 6), within which rectangular coil 71 rests. The protruding end of rectangular coil 70a is manufactured continuous with tubular wiring 53 (see FIG. 6). The one-piece continuous design eliminates an additional weld or connection at the actual electrode. The elimination of the weld in this area is significant, because it eradicates the possibility of two dissimilar metals interacting within the ionic environment and adding an erroneous signal to the system. Removing the weld also eliminates any intermetalics formed during the weld.

While particular embodiments of the present invention have been shown and described, modifications may be made, and it is therefore intended in the appended claims to cover all such changes and modifications that fall within the true spirit and scope of the invention.

What is claimed is:

1. An implantable electrocardiographic data collection system for recording electrocardiographic data, the system comprising:
   a hermetically sealed case;
   a plurality of subcutaneous spiral electrodes forming an array, mounted in a recessed casing formed about a periphery surface of the case; and
   signal processing circuitry inside the case coupled to the electrodes via a connector feedthrough assembly in contact with amplifiers in a microprocessor circuitry.

2. The system of claim 1 wherein said recessed casing is composed of a polymer.

3. The system of claim 2 wherein the case includes walls into which body fluid is allowed to flow so that the body fluid is above and around the spiral electrodes and is contained in the casing by a small circumferential well constructed into the base of said recessed casing.

4. The system according to claim 3 wherein the spiral electrodes include spiral coils consisting of materials selected from the group of platinum, platinum alloys and platinum group of metals with or without alloy components.

5. The system according to claim 3 wherein said spiral electrodes include a spiral coil forming a proximal end of a continuous wire that upon egress from said recessed casing, is insulated by tubular insulative materials.

6. The system according to claim 5 wherein said insulated tubular insulative material feeds into channels located on the inner arc on a compliant surround.

7. The system according to claim 5 wherein a distal end of said continuous wire is welded to connector feedthrough assembly in contact with amplifiers in a microprocessor secretary.

8. Apparatus for leadless acquistion of electrocardiographic data using an array of subcutaneous spiral electrodes to detect cardiac depolarization signals that are very small, and signals with low slew rates, the system comprising:
   a hermetically sealed case;
   a plurality of spiral subcutaneous electrodes attached to a pulse generator by a compliant surround, mounted in the periphery surface of the case; and
   signal processing circuitry inside the case and electrically coupled to the plurality of electrodes to detect cardiac signals and provide electrocardiographic data.

9. The apparatus of claim 8 wherein the surface of said plurality of spiral electrodes is isolated from direct contact with body tissue and moving body fluids.

10. The apparatus of claim 9 wherein said surface of said electrodes is treated with electrode coating such as platinum black or titanium nitride to enhance signal conducting and depolarization properties.

11. The apparatus of claim 9 wherein said plurality of said electrodes include a continuous wire connection without weld or bonds on the electrode surface.

12. The plurality of electrodes of claim 9 wherein said electrodes are anchored in the case, free of any chemical bonding, in a recessed section of the case.

13. The apparatus of claim 12 wherein a portion of said electrode that is covered by said recessed section is minimal to prevent potential excursions caused by fluid creep or by trapped oxygen or hydrogen gradient.

14. The apparatus of claim 9 wherein said electrodes include a coiled electrode design in a rectangular configuration.

15. The apparatus of claim 9, wherein the case includes a recessed section having a well, and wherein said electrodes include a flat plated electrode embedded within the well of said recessed section.

16. The apparatus of claim 15 wherein said flat plated electrode is stabilized against electromagnetic potential disturbances by structuring a bottom of the well of said recessed section patterned with a cross-hatch structure with elevations and depressions formed to have a minimum contact area between the plate and the polymer used in the recessed section.

17. The apparatus of claim 16 wherein said cross-hatch structure supports said electrode and enables fluid contact with the underside of said electrode surface.

18. Apparatus of claim 9 wherein a protective cap is placed to allow fluid to ingress to the active electric element wherein said protective cap is placed over the recessed section containing said flat electrode.

19. The apparatus of claim 18 wherein said cap is structured to apply pressure on said electrode for pressing against said cross-hatch structure of the recessed section to prevent motion of said electrode.

20. The apparatus of claim 19 wherein said cap is structured to dampen external fluid motion that might otherwise reach said electrode and cause electroconnectic transience.

21. The apparatus of claim 9 wherein said electrode surface is treated with a coating to protect from contamination during handling.

22. The apparatus of claim 21 wherein said coating includes dexamethasone sodium phosphates to provide protection to enhance the wetting of the electrode surface after implant.

23. The apparatus of claim 22 wherein conductive hydro gels are applied to said electrode surface to protect from damage during handling and prevent contamination.

24. The apparatus of claim 8 wherein a spacing of said electrodes around a compliant surround provides maximum electrode spacing.

25. The apparatus of claim 24 wherein said spacing maintains a maximum average signal using two equal vectors.

26. The apparatus of claim 25 wherein said spacing of said equal vectors includes a 90° angle vector.

* * * * *